US00PP12513P2

(12) United States Plant Patent
Vandenberg et al.

(10) Patent No.: US PP12,513 P2
(45) Date of Patent: Apr. 2, 2002

(54) CHRYSANTHEMUM PLANT NAMED 'YOHARTFORD'

(75) Inventors: Cornelis P. Vandenberg, Salinas, CA (US); Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/594,754

(22) Filed: Jun. 16, 2000

(51) Int. Cl.[7] ..... A01H 5/00
(52) U.S. Cl. ..... Plt./286

(58) Field of Search ..... Plt./286, 297

*Primary Examiner*—Howard J. Locker
(74) *Attorney, Agent, or Firm*—C. A. Whealy

(57) ABSTRACT

A distinct cultivar of Chrysanthemum plant named 'Yohartford', characterized by its upright, somewhat spreading, compact, and uniformly mounded plant habit; strong, dark green foliage; uniform flowering response; early flowering, eight-week response time, very large sincle anemone-type inflorescences that are about 11.8 cm in diameter, lavender pink-colored ray florets and yellow-tipped disc florets; and good postproduction longevity with inflorescences maintaining good substance and color for about three weeks in an interior environment.

1 Drawing Sheet

BACKGROUND OF THE INVENTION

The present Invention relates to a new and distinct cultivar of Chrysanthemum plant, botanically known as *Dendranthema grandiflora* and hereinafter referred to by the cultivar name Yohartford.

The new Chrysanthemum is a product of a planned breeding program conducted by the Inventors in Salinas, Calif. and Fort Myers, Fla. The objective of the breeding program is to create new potted Chrysanthemum cultivars with desirable inflorescence form and floret colors and good postproduction longevity.

The new Chrysanthemum originated from a cross made by the Inventors in February, 1995, in Salinas, Calif., of a proprietary Chrysanthemum seedling selection identified as YB-4470 as the female, or seed, parent with the Chrysanthemum cultivar Blush, disclosed in U.S. Plant Pat. No. 7,985 as the male, or pollen, parent. The new Chrysanthemum was discovered and selected by the Inventors in April, 1996, as a single flowering plant within the progeny of the stated cross grown in a controlled environment in Fort Myers, Fla. The selection of this plant was based on its desirable inflorescence form and floret colors and good postproduction longevity.

Asexual reproduction of the new Chrysanthemum by vegetative tip cuttings was first conducted in Fort Myers, Fla. in June, 1996. Asexual reporduction by cuttings has shown that the unique features of this new Chrysanthemum are stable and reproduced true to type in successive generations.

SUMMARY OF THE INVENTION

The cultivar Yohartford has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yohartford'. These characteristics in combination distinguish 'Yohartford' as a new and distinct Chrysanthemum:

1. Upright, somewhat spreading, compact, and uniformly mounded plant habit.

2. Strong, dark green foliage.

3. Uniform flowering response.

4. Early flowering, eight-week response time.

5. Can be grown as a disbud or spray-type.

6. Very large single anemone-type inflorescences that are about 11.8 cm in diameter.

7. Lavender pink-colored ray florets and yellow-tipped disc florets.

8. Good postproduction longevity with inflorescences maintaining good substance and color for about three weeks in an interior environment.

Plants of the new Chrysanthemum differ from plants of the cultivar, Dark Pink Yoblush, disclosed in U.S. Plant Pat. No. 11,995, in the following characteristics:

. Plants of the new Chrysanthemum have single anemone-type inflorescences whereas plants of the cultivar Dark Pink Blush have single daisy-type inflorescences.

2. Plants of the new Chrysanthemum are more compact than plants of the cultivar Dark Pink Blush.

3. Ray florets of plants of the new Chrysanthemum twist more with age than ray florets of the plants of the cultivar Dark Pink Blush.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type. Colors in the photographs may differ from the color values cited in the detailed botanical description which more accurately describe the actual colors of the new Chrysanthemum.

The photograph at the top of the sheet comprises a top perspective view of a typical flowering plant of 'Yohartford'.

The photograph at the bottom of the sheet comprises a close-up view of typical inflorescences of the cultivar Yohartford.

DETAILED BOTANICAL DESCRIPTION

In the following description, color references are made to The Royal Horticulatural Society Colour Chart except where general terms of ordinary dictionary significance are used. The following observations and measurements describe plants grown and flowered during the Spring in Salinas, Calif. and Leamington, Ontario, Canada, under greenhouse conditions which approximate those generally used in commercial potted Chrysanthemum production. Four unrooted cuttings were directly stuck in a 15-cm container and pinched once. Plants used for this description were grown as disbudded-types. Measurements and numerical values represent averages of typical flowering plants.

Botanical classification: *Dendranthema grandiflora* cultivar Yohartford.

Commercial classification: Single anemone-type potted Chrysanthemum.

Parentage:

*Female, or seed, parent.*—Proprietary Chrysanthemum seedling selection identified as YB-4470.

*Male, or pollen, parent.*—*Dendranthema grandiflora* cultivar Blush, disclosed in U.S. Plant Pat. No. 7,985.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Herbaceous single anemone-type potted Chrysanthemum that can be grown as a disbud or spray-type, but typically grown as a disbud. Inverted triangle; stems mostly upright and somewhat outwardly spreading giving a uniformly mounded appearance to the plant. About three lateral branches develop after removal of terminal apex (pinching). Moderately vigorous.

*Plant height.*—About 23 cm.

*Plant width.*—About 34 cm.

*Lateral branches.*—Length: About 13 cm. Diameter: About 3.5 mm. Internode length: About 1.3 cm. Strength: Flexible, but strong. Texture: Pubescent. Color: 144A.

*Foliage description.*—Arrangement: Alternate. Quantity per lateral stem: About 11. Length: About 4.9 cm. Width: About 4.2 cm. Apex: Mucronate. Base: Mostly truncate. Margin: Palmately lobed, sinuses between lateral lobes mostly convergent to overlapping. Texture: Upper and lower surfaces with very fine pubescence: veins prominent on lower surface. Color: Young foliage upper surface: 147A. Young foliage lower surface: 147B. Mature foliage upper surface: 147A. Mature foliage lower surface: 147B. Venation upper surface: 147B. Venation lower surface: 147B. Petiole length: About 2.2 cm. Petiole diameter: About 3 mm. Petiole color: 147B to 147C.

Inflorescence description:

*Appearance.*—Single anemone-type inflorescence form with elongated oblong-shaped ray florets. Inflorescences borne on terminals above foliage. Disk and ray florets arranged acropetally on a capitulum. Not fragrant.

*Flowering response.*—Under natural conditions, plants flower in the autumn/winter in the Northern Hemisphere. At other times of the year, inflorescence initiation and development can be induced under short day/long night conditions (at least 13.5 hours of darkness). Plants exposed to three weeks of long day/short night conditions after planting followed by photoinductive short day/long night conditions flower about eight weeks later; early flowering.

*Postproduction longevity.*—Inflorescences maintain good color and substance for about three weeks in an interior environment.

*Quantity of inflorescences.*—Can be grown as a disbud or spray-type, however typically grown as a disbud with one inflorescence per lateral stem; about three inflorescences per plant.

*Inflorescence bud.*—Height: About 7 mm. Diameter: About 7 mm. Color: Close to 137A.

*Inflorescence size.*—Diameter: About 11.8 cm. Depth (height): About 3.1 cm. Diameter of disc: About 4.4 cm. Receptacle diameter: About 8 mm.

*Ray florets.*—Shape: Elongated-oblong. Orientation: Initially upright, then about perpendicular to peduncle; with development, some twisting and somewhat reflexed. Length: About 5.5 cm. Width: About 1.2 cm. Apex: Mostly mammilate to dentate. Base: Attenuate; very short corolla tube. Margin: Entire. Texture: Smooth, glabrous, satiny. Number of ray florets per inflorescence: About 28; one row. Color: When opening, upper surface: 77B. When opening, lower surface: 77C to 77D. Fully opened, upper surface: 77B to 77C or close to 80C; fading to 77D with subsequent development. Fully opened, lower surface: 77C to 77D to 75D.

*Disc florets.*—Shape: Enlarged, flared. Apex: Five-pointed, fringed appearance. Length: About 2.1 cm. Width: Apex, about 6 mm; base, about 1 mm. Number of disc florets per inflorescence: About 210. Color: Immature: Close to 154A to 3A to 5A. Mature: Apex: Tipped with 3A to 9A to 12A. Midsection: Throat, pale 58A to 77A to 77B; tube, 77C to 77D. Base: Close to 151A.

*Reproductive organs.*—Androecium: Present on disc florets only. Anther color: 9A. Pollen amount: None observed. Gynoecium: Present on both ray and disc florets.

Disease resistance: Resistance to pathogens common to Chrysanthemums has not been observed on plants grown under commercial greenhouse conditions.

Seed production: Seed production has not been observed.

It is claimed:

1. A new and distince cultivar of Chrysanthemum plant named 'Yohartford', as illustrated and described.

* * * * *

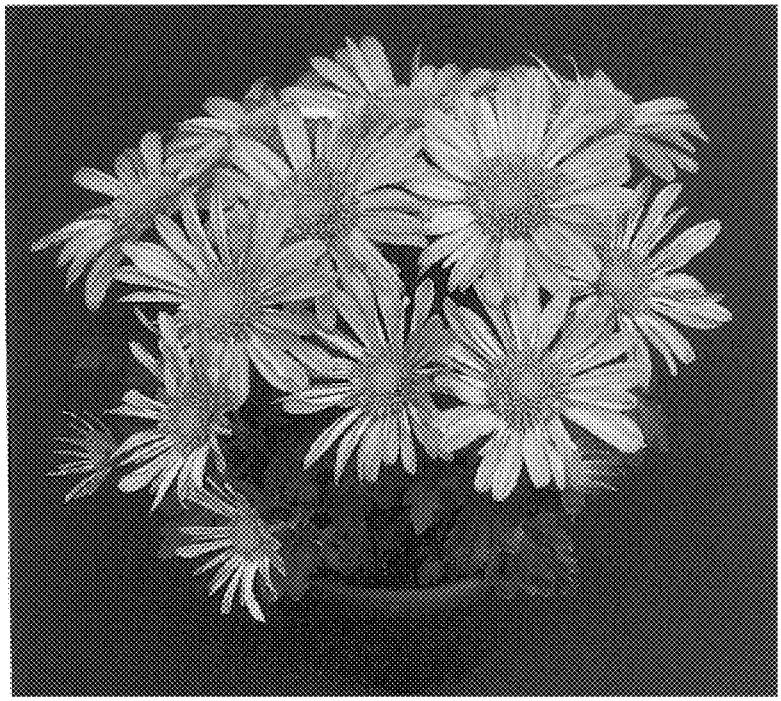
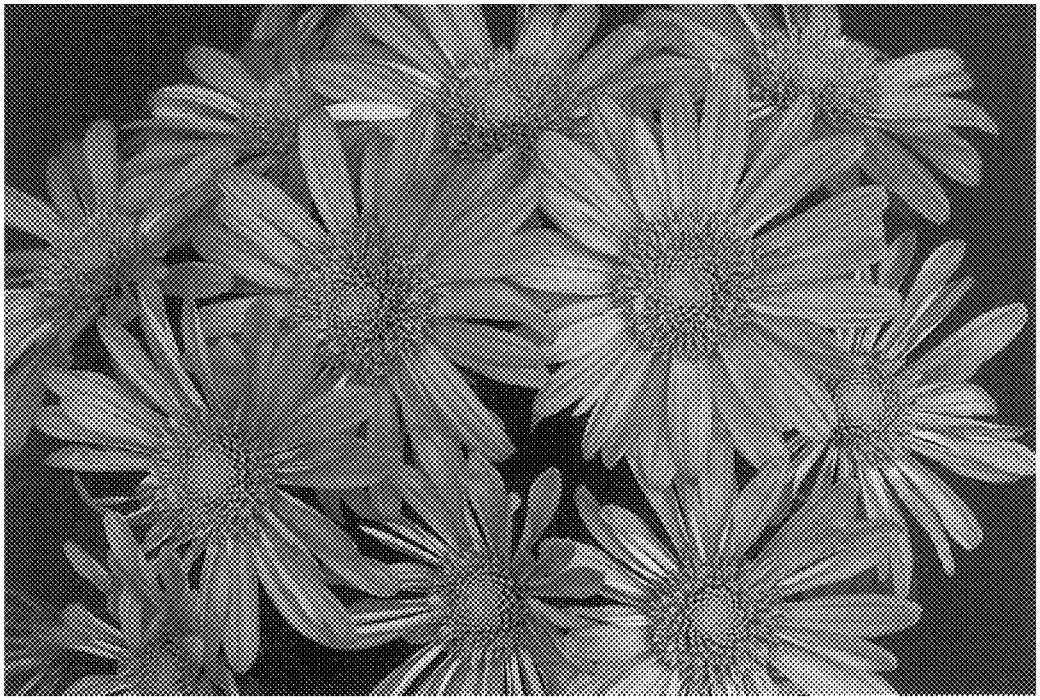

UNITED STATES PATENT AND TRADEMARK OFFICE

CERTIFICATE OF CORRECTION

PATENT NO. : PP 12,513 P2
DATED : April 2, 2002
INVENTOR(S) : Vandenberg et al.

It is certified that error appears in the above-identified patent and that said Letters Patent is hereby corrected as shown below:

Title page,
Item [*] Notice, delete the phrase "by 0 days" and insert -- by 15 days --

Signed and Sealed this

Eleventh Day of May, 2004

JON W. DUDAS
*Acting Director of the United States Patent and Trademark Office*